(12) United States Patent
Miyamura et al.

(10) Patent No.: US 10,125,107 B1
(45) Date of Patent: Nov. 13, 2018

(54) CARBOXYLIC ACID ESTER COMPOUND HAVING POLYMERIZABLE FUNCTIONAL GROUP AND FLUORINE ATOM GROUP, AND METHOD FOR PRODUCING SAME

(71) Applicant: UNIMATEC CO., LTD., Tokyo (JP)

(72) Inventors: Takuhiro Miyamura, Ibaraki (JP); Keisuke Kokin, Ibaraki (JP)

(73) Assignee: UNIMATEC CO., LTD., Tokyo (JP)

( * ) Notice: Subject to any disclaimer, the term of this patent is extended or adjusted under 35 U.S.C. 154(b) by 0 days.

(21) Appl. No.: 15/778,937

(22) PCT Filed: Dec. 16, 2016

(86) PCT No.: PCT/JP2016/087667
§ 371 (c)(1),
(2) Date: May 24, 2018

(87) PCT Pub. No.: WO2017/110698
PCT Pub. Date: Jun. 29, 2017

(30) Foreign Application Priority Data

Dec. 25, 2015 (JP) .................................. 2015-253135

(51) Int. Cl.
*C07C 69/80* (2006.01)
*C07C 67/14* (2006.01)
*C07C 69/708* (2006.01)
*C07D 251/34* (2006.01)
*C08F 220/18* (2006.01)

(52) U.S. Cl.
CPC ............ *C07D 251/34* (2013.01); *C07C 67/14* (2013.01); *C07C 69/708* (2013.01); *C07C 69/80* (2013.01); *C08F 220/18* (2013.01)

(58) Field of Classification Search
CPC ....... C07C 69/708; C07C 69/80; C07C 67/14; C07D 251/34

USPC .......................................... 544/221; 558/283
See application file for complete search history.

(56) References Cited

U.S. PATENT DOCUMENTS 9,604,918 B2 * 3/2017 Miyamura .............. C08F 20/24

FOREIGN PATENT DOCUMENTS

JP S58-194839 A 11/1983

OTHER PUBLICATIONS

International Search Report and Written Opinion received in connection with international application No. PCT/JP2016/087667; dated Mar. 7, 2017, (with English translation of the international search report).

* cited by examiner

*Primary Examiner* — Venkataraman Balasubramanian
(74) *Attorney, Agent, or Firm* — The Marbury Law Group, PLLC

(57) ABSTRACT

Provided are a fluorine-containing monomer capable of being dissolved in a general organic solvent such as a hydrocarbon solvent and simultaneously having excellent water and oil repellency, and a method for producing the fluorine-containing monomer. The fluorine-containing monomer is a carboxylic acid ester compound having a polymerizable functional group and a fluorine atom group, represented by the following general formula: $C_aF_{2a+1}O-(C_bF_{2b}O)_c-C_2F_4COOR$. The method is a process for producing the carboxylic acid ester compound, characterized by that any one of an isocyanulate derivative, a phthalic acid derivative and a cycloalkane dialcohol modified (meth) acrylate each having a terminal hydroxyl group is made to react with a perfluoropolyether carboxylic acid halide.

4 Claims, No Drawings

CARBOXYLIC ACID ESTER COMPOUND HAVING POLYMERIZABLE FUNCTIONAL GROUP AND FLUORINE ATOM GROUP, AND METHOD FOR PRODUCING SAME

FIELD OF INVENTION

The present invention relates to a carboxylic acid ester compound having a polymerizable functional group and a fluorine atom group, and a method for producing the carboxylic acid ester compound.

BACKGROUND ART

Generally, a compound having a fluorine atom in the molecule is excellent in thermal and chemical stability, and simultaneously provided with good optical and surfactant properties. The characteristics allow a compound having a fluorine atom in the molecule to be widely applied to, for example, an antireflection film for a monitor screen, a cladding agent for optical fibers and a coating agent.

The compound having a fluorine atom in the molecule includes, for example, monomers such as a fluorine-containing ester compound and a fluorine-containing ether compound. A homopolymer and a copolymer obtained from those monomers having a variety of chemical structures have been developed and used in the above described application.

Patent Document 1 discloses a fluorine-containing acrylic acid ester shown by the following general formula as a representative example of a fluorine-containing ester compound.

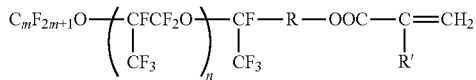

(where R is a bivalent organic linking group; R' is a hydrogen atom or a methyl group; n is 0 or a positive integer; and m is a positive integer.)

DOCUMENTS OF PRIOR ART

Patent Documents

Patent Document 1: Japanese Unexamined Patent Application Publication No. Sho 58-194839

SUMMARY OF INVENTION

Problems to be Solved by Invention

However, such a fluorine-containing monomer is hard to be dissolved in a general and inexpensive solvent, but dissolved only in a fluorine based solvent. This property causes a drawback of a limited use thereof due to price and legal regulation issues.

Actually, a fluorine-containing monomer disclosed in Patent Document 1 has good oil and water repellency, while the monomer is hard to be dissolved in a general solvent, causing a drawback of phase-separation when mixed with other resins.

The present invention has been made in view of the above drawbacks. Therefore, an object of the present invention is to provide a fluorine-containing monomer capable of being dissolved in a general organic solvent such as a hydrocarbon based solvent and simultaneously having excellent oil and water repellency, and a method for producing the fluorine-containing monomer.

Means for Solving Problems

The present inventors have investigated introduction of various hydrocarbon groups and functional groups into a monomer having a fluorine atom group (i.e., functional group having many fluorine atoms) and a polymerizable functional group (i.e., unsaturated group) in order to increase the solubility of a fluorine-containing monomer in a general organic solvent such as a hydrocarbon based solvent. Further, the present inventors have investigated chemical structures of the fluorine atom group and binding modes of each functional group.

As a result, the present inventors have found out that a fluorine-containing monomer having excellent solubility in a general organic solvent and miscibility with a curable resin can be produced by using an isocyanulate group, a phthalic acid derivative or a cyclic aliphatic group as a hydrocarbon group and a functional group, thereby affording a monomer a specific chemical structure where the hydrocarbon group and the functional group are arranged in an intermediate position between the fluorine atom group and the polymerizable functional group.

Further, the present inventors have found out that the fluorine-containing monomer can be easily produced in a single step by using raw materials of a perfluorocarboxylic acid halide and an acrylate having a terminal hydroxyl group.

The above investigations have been repeatedly conducted, resulting in accomplishment of the present invention. In summary, the present invention has the following aspects.

A carboxylic acid ester compound of the present invention is represented by the general formula [I] having a polymerizable functional group and a fluorine atom group.

   [I]

where a is an integer from 1 to 3; b is an integer from 1 to 4; c is an integer from 0 to 50; and R is represented by the following general formula [II],

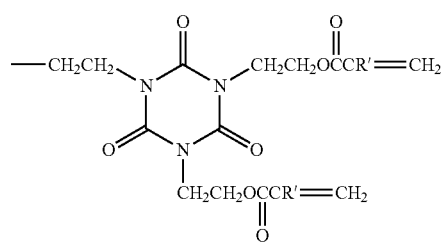

or represented by the following general formula [III],

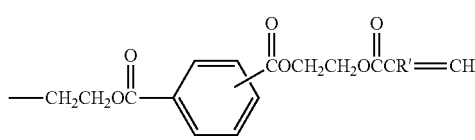

or represented by the following general formula [IV],

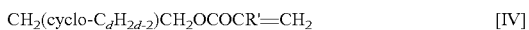

(where R' is a hydrogen atom or a methyl group; and d is an integer from 3 to 6.)

Further, a method for producing a carboxylic acid ester compound of the present invention is a process for preparing a carboxylic acid ester compound represented by the general formula [I]. Herein, the method is characterized by that any one of an isocyanulate derivative represented by the general formula [V], a phthalic acid derivative represented by the general formula [VI] and a cycloalkane dialcohol modified (meth)acrylate represented by the general formula [VII] is made to react with a perfluoropolyether carboxylic acid halide represented by the general formula [VIII].

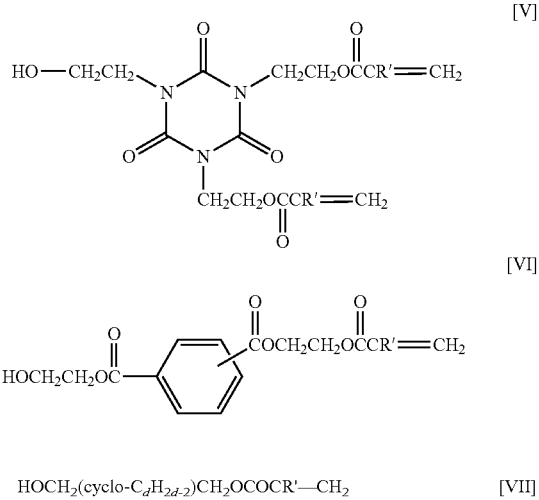

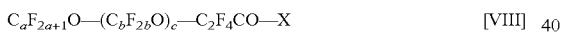

(where R' is a hydrogen atom or a methyl group; and d is an integer from 3 to 6.)

$C_aF_{2a+1}O—(C_bF_{2b}O)_c—C_2F_4CO—X$     [VIII]

(where X is a halogen atom; a is an integer from 1 to 3; b is an integer from 1 to 4; and c is an integer from 0 to 50.)

Effect of Invention

A fluorine-containing monomer of the present invention is capable of being dissolved in a general organic solvent, and simultaneously having excellent oil and water repellency. Further, a method for producing a fluorine-containing monomer of the present invention is capable of preparing the fluorine-containing monomer by a simple step in a high yield.

EMBODIMENTS FOR CARRYING OUT INVENTION

Hereinafter, embodiments of the present invention will be described in detail. Here, it should be noted that a scope of the present invention is not limited to the specific examples described below.

A method for producing a carboxylic acid ester compound of the present invention is characterized by that an acrylate having a terminal hydroxyl group is made to react with a carboxylic acid halide having a perfluoropolyether group.

More specifically, the method of the present invention is a process for preparing a fluorine-containing polymerizable monomer via making any one of an isocyanulate ethyleneoxide modified di(meth)acrylate, a phthalic acid hydroxyethyl modified (meth)acrylate and a cycloalkane dimethanol modified (meth)acrylate react with a carboxylic acid halide having a perfluoropolyether group in the presence of a hydrogen halide scavenger.

Next, a reaction of the present invention will be described in detail.

The reaction of the present invention is a process for preparing a carboxylic acid ester compound represented by the general formula [I] having a polymerizable functional group and a fluorine atom group via making any one of an isocyanulate derivative represented by the general formula [V], a phthalic acid derivative represented by the general formula [VI] and a cycloalkane dialcohol modified (meth)acrylate represented by the general formula [VII] react with a carboxylic acid halide having a perfluoropolyether group represented by the general formula [VIII].

Here, the isocyanulate derivative is represented by the following general formula [V].

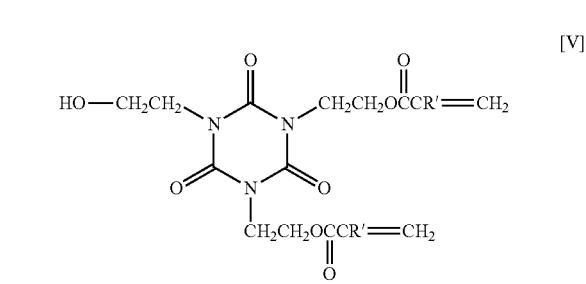

(where R' is a hydrogen atom or a methyl group.)

Further, the phthalic acid derivative is represented by the following general formula [VI].

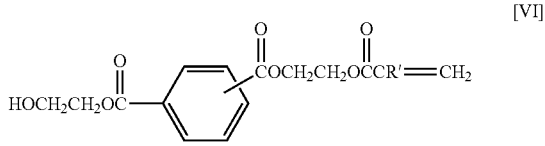

(where R' is a hydrogen atom or a methyl group.)

Moreover, the cycloalkane dialcohol modified (meth)acrylate is represented by the following general formula [VII].

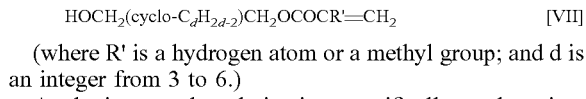

(where R' is a hydrogen atom or a methyl group; and d is an integer from 3 to 6.)

As the isocyanulate derivative, specifically used are isocyanuric acid ethyleneoxide modified diacrylate, and isocyanuric acid ethyleneoxide modified dimethacrylate or the like.

As the phthalic acid derivative, specifically used are phthalic acid hydroxyethyl modified acrylate, phthalic acid hydroxyethyl modified methacrylate, isophthalic acid hydroxyethyl modified acrylate, isophthalic acid hydroxyethyl modified methacrylate, terephthalic acid hydroxyethyl modified acrylate, and terephthalic acid hydroxyethyl modified methacrylate or the like.

As the cycloalkane dialcohol modified (meth)acrylate, specifically used are cyclopropane dimethanol modified acrylate, cyclobutane dimethanol modified acrylate, cyclopentane dimethanol modified acrylate, cyclohexane dimethanol modified acrylate, cyclopropane dimethanol modified methacrylate, cyclobutane dimethanol modified methacrylate, cyclopentane dimethanol modified methacrylate, and cyclohexane dimethanol modified methacrylate or the like.

The perfluoropolyether carboxylic acid halide is represented by the following general formula [VIII].

$$C_aF_{2a+1}O—(C_bF_{2b}O)_c—C_2F_4CO—X \qquad [VIII]$$

(where X is a halogen atom; a is an integer from 1 to 3; b is an integer from 1 to 4; and c is an integer from 0 to 50.)

As the perfluoropolyether carboxylic acid halide, specifically used are the followings.

(a) 2,4,4,5,7,7,8,10,10,11,13,13,14,16,16,17,17,18,18,18-eicosafluoro-3,6,9,12,15-pentaoxa-2,5,8,11,14-pentakis (trifluoromethyl)octadecanoyl fluoride;

(b) 2,4,4,5,7,7,8,10,10,11,13,13,14,16,16,17,17,17-octadecafluoro-3,6,9,12,15-pentaoxa-2,5,8,11,14-pentakis (trifluoromethyl)heptadecanoyl fluoride;

(c) 2,4,4,5,7,7,8,10,10,11,13,13,14,16,16,16-hexadecafluoro-3,6,9,12,15-pentaoxa-2,5,8,11,14-pentakis(trifluoromethyl) hexadecanoyl fluoride;

(d) 2,4,4,5,7,7,8,10,10,11,13,13,14,16,16,17,19,19,20,22, 22,23,25,25,26,28,28,29,29,30,30,30-dotriacontafluoro-3,6,9,12,15,18,21,24,27-nonaoxa-2,5,8,11,14,17,20,23, 26-nonakis(trifluoromethyl) triacontanoyl fluoride;

(e) 2,4,4,5,7,7,8,10,10,11,13,13,14,16,16,17,19,19,20,22, 22,23,25,25,26,28,28,29,29,29-triacontafluoro-3,6,9,12, 15,18,21,24,27-nonaoxa-2,5,8,11,14,17,20,23,26-nonakis (trifluoromethyl) nonacosanoyl fluoride;

(f) 2,4,4,5,7,7,8,10,10,11,13,13,14,16,16,17,19,19,20,22,22, 23,25,25,26,28,28,28-octacosafluoro-3,6,9,12,15,18,21, 24,27-nonaoxa-2,5,8,11,14,17,20,23,26-nonakis(trifluoromethyl) octacosanoyl fluoride;

(g) 2,2,3,3,5,5,6,6,7,7,9,9,10,10,11,11,13,13,14,14,15,15, 15-tricosafluoro-4,8,12-trioxapentadecanoyl fluoride; and (h) 2,2,3,3,5,5,6,6,7,7,9,9,10,10,11,11,13,13,14,14,15,15, 17,17,18,18,19,19,21,21,22,22,23,23,25,25,26,26,27,27, 29,29,30,30,31, 31,31-heptatetracontafluoro-4,8,12,16, 20,24,28-heptaoxahen-triacontanoyl fluoride.

Among those compounds, preferably used are:

(a) 2,4,4,5,7,7,8,10,10,11,13,13,14,16,16,17,17,18,18,18-eicosafluoro-3,6,9,12,15-pentaoxa-2,5,8,11,14-pentakis (trifluoromethyl)octadecanoyl fluoride; and (d) 2,4,4,5,7,7,8,10,10,11,13,13,14,16,16,17,19,19,20,22, 22,23,25,25,26,28,28,29,29,30,30,30-dotriacontafluoro-3,6,9,12,15,18,21,24,27-nonaoxa-2,5,8,11,14,17,20,23, 26-nonakis(trifluoromethyl) triacontanoyl fluoride or the like.

The above described perfluoropolyether carboxylic acid halides (a) to (h) are shown by the following chemical formulae.

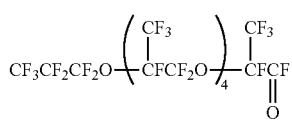
(a)

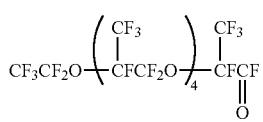
(b)

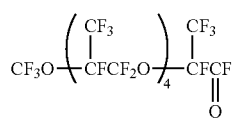
(c)

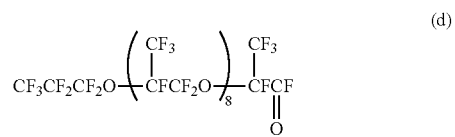
(d)

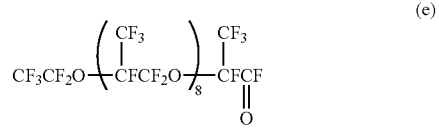
(e)

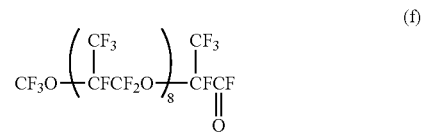
(f)

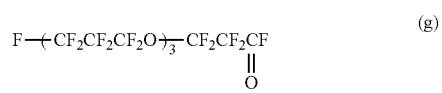
(g)

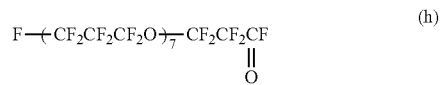
(h)

The reaction of the acrylate having a terminal hydroxyl group with the perfluoropolyether carboxylic acid halide is conducted by a dehydrohalogenated condensation reaction using usually 1.1-fold to 2-fold mol of the acrylate having a terminal hydroxyl group per the carboxylic acid halide having a perfluoropolyether group.

As a reaction solvent, any solvents can be used as long as those solvents are inactive to the reaction. Generally, a fluorine based solvent is used therefor. More specifically, such a solvent includes Asahiklin™ AK225 (Asahi Glass Co., Ltd.), Asahiklin™ AE3000 (Asahi Glass Co., Ltd.), Novec™ HFE (Sumitomo 3M Co., Ltd.), Vertrel™ XF (Du Pont), and Fluorinert™ FC-72 (Sumitomo 3M Co., Ltd) or the like. Preferable one is Asahiklin™ AK225 (Asahi Glass Co., Ltd.).

Since the reaction is a dehydrohalogenated condensation reaction, it is preferable to conduct the reaction in the presence of a hydrogen halide scavenger. As a hydrogen halide scavenger, generally used are alkaline metal fluorides such as lithium fluoride, sodium fluoride and potassium fluoride; organic amine compounds such as triethylamine and tributylamine. Further, among those compounds, an alkaline metal fluoride such as sodium fluoride and triethylamine are preferably used in view of the ability of retaining generated hydrogen fluoride and the costs. A rate of the hydrogen halide scavenger used in the reaction is preferably in the range from 2-fold to 8-fold mol per the perfluoropolyether carboxylic acid halide, more preferably 2.1-fold to 3.0-fold mol.

The carboxylic acid ester compound thus obtained has a polymerizable functional group. Thus, it is preferable to conduct the reaction by adding methoquinone (i.e., p-methoxyphenol) or hydroquinone working as a polymerization inhibitor in the reaction system.

The carboxylic acid ester compound of the present invention thus prepared as mentioned above includes, for example, the following compounds.

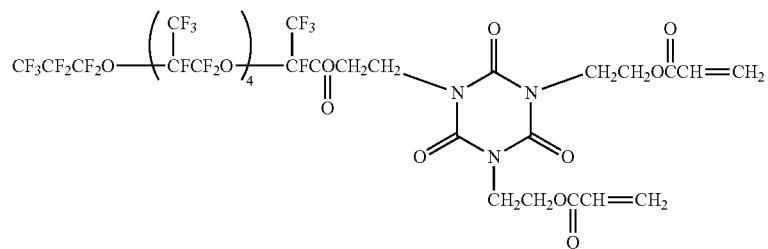
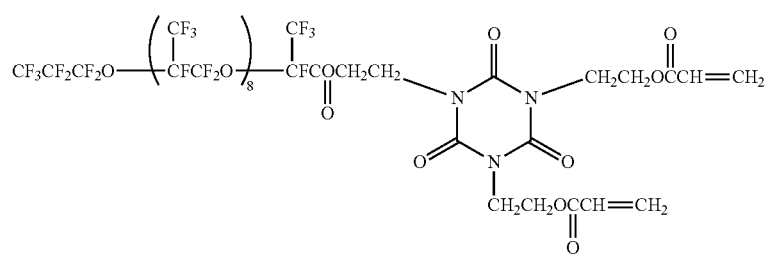
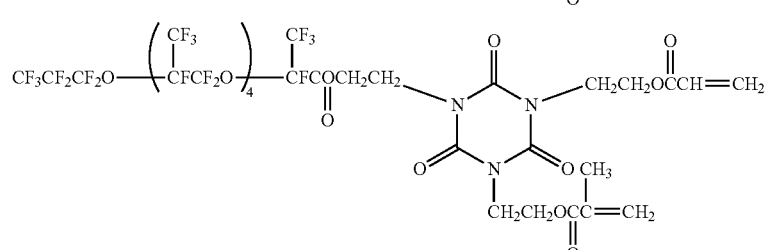
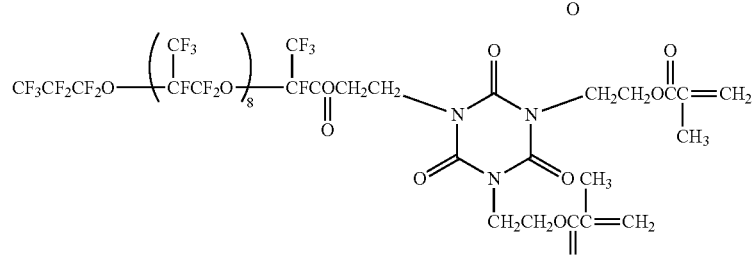
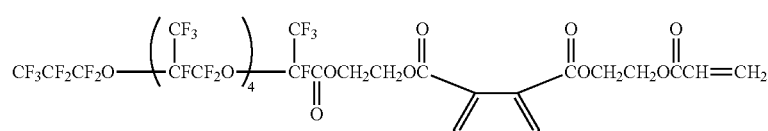
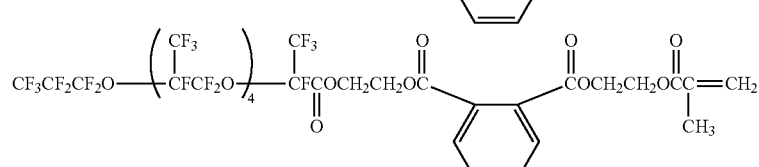
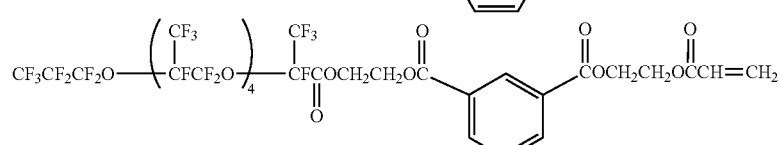
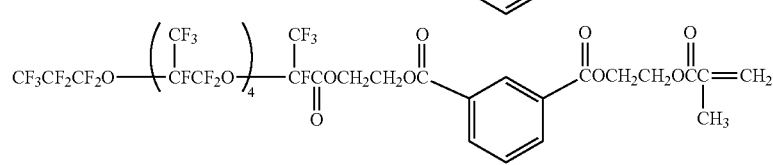

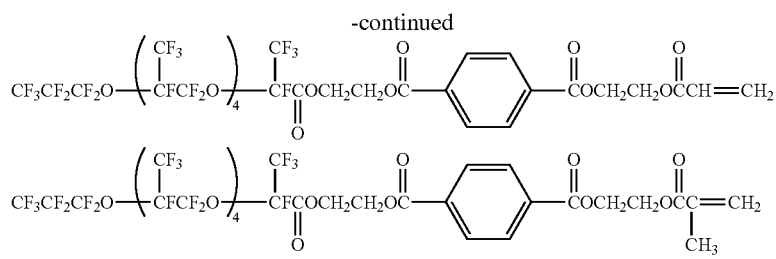

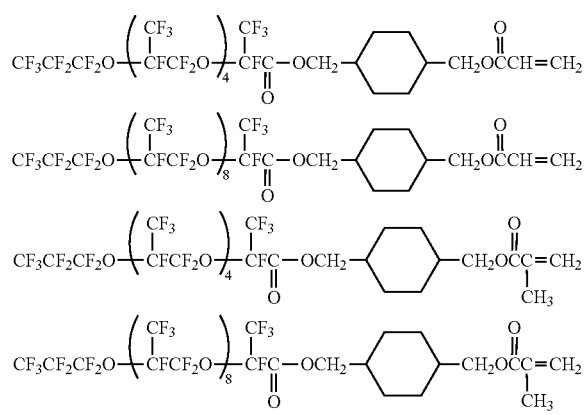

A fluorine-containing polyether (di)(meth)acrylate that is a carboxylic acid ester compound of the present invention has a polymerizable functional group, a fluorine atom group, a hydrocarbon group and a functional group in the molecule. Therefore, the carboxylic acid ester compound has excellent solubility in a general organic solvent and miscibility with a curable resin without harming the oil and water repellency, fingerprint resistance and antifouling property.

Further, the carboxylic acid ester compound has many fluorine atoms in the molecule, which affords excellent thermal and chemical stability as well as good optical and surfactant properties. Herein, a general organic solvent includes, for example, hydrocarbon based solvents such as an aliphatic-, an aromatic-, a ketone-, and an ether-type solvent; an amine based solvent; and a sulfur based solvent.

Moreover, a carboxylic acid ester compound of the present invention is curable by being exposed to energy beams such as visible light, ultraviolet light, and electron beams. Thus, the compound is applicable to a photosensitive curable ink, paint, and electron beam curable adhesive agent.

Furthermore, the compound can be prepared as a multifunctional monomer, which allows formation of crosslinking in the three dimensional structure. This enables the compound applicable to a variety of crosslinking agents and modifiers. As a result, it becomes possible to improve or enhance physical properties such as hardness, strength, thermo resistance, weather resistance and chemical resistance.

Here, the carboxylic acid ester compound of the present invention has relatively large contents of fluorine atoms in the molecule, which gives the compound a low refractive index. Therefore, the compound may be used for an antireflection film of a display, and a cladding material of optical fibers. Further, the surfactant property thereof allows use in a variety of releasing coating agents, surface modifiers, and water and oil repellant agents.

EXAMPLES

Hereinafter, Examples will be described more specifically. However, the present invention is not limited to those Examples.

Example 1

Isocyanuric acid ethylene oxide modified diacrylate (157 g, 0.43 mol) (TOUAGOSEI CO., LTD, Aronix™ M-215) was dissolved in a mixed solvent of HCFC-225ca/HCFC-225cb (300 g; Asahi Glass Co., Ltd, Asahiklin™ AK225), and NaF (44.1 g, 1.05 mol) was added thereto. Then, with stirring the resultant mixture, a fluorine-containing polyether carboxylic acid fluoride (350 g, 0.35 mol) was added dropwise to the mixture, and the mixture was stirred for 2 hrs. The reaction end was determined by NMR via confirming disappearance of the peak of carboxylic acid fluoride. The product was yielded in 401 g, 85.2% yield, and 97.6% purity.

The reaction formula of Example 1 is shown below.

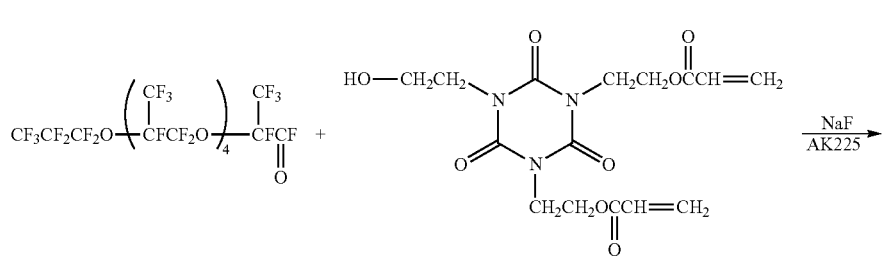

-continued

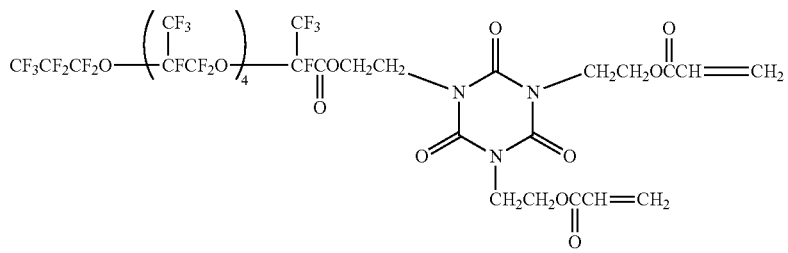

The results of NMR identification on the product of Example 1 are summarized as follows. It was confirmed that the above described reaction of Example 1 proceeded to give a carboxylic acid ester compound of the present invention having the following chemical structure in a high yield.

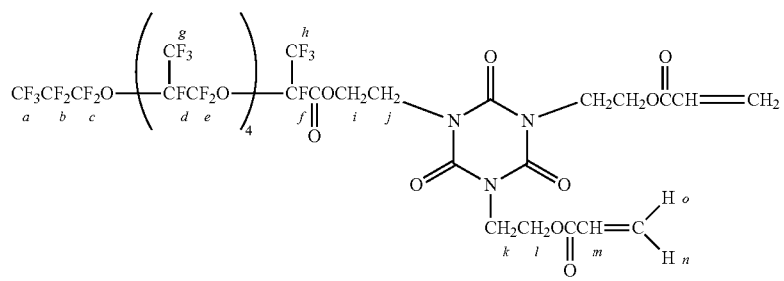

$^{19}$F-NMR [$(CD_3)_2CO$, $C_6F_6$]

δ (ppm): −144.0: d, −130.5: f, −128.8: b, −84.5 to −77.5: a, c, e, g, h $^1$H-NMR [$(CD_3)_2CO$]

δ (ppm): 3.6: j, 3.9: i, 4.1: l, 4.2: k, 5.8: o, 6.0: n, 6.2: m

Example 2

Phthalic acid hydroxyethyl modified acrylate (120 g, 0.41 mol) (Kyoeisha Chemical Co., Ltd., Light Acrylate™ HOA-MPE(N)) was dissolved in a mixed solvent of HCFC-225ca/HCFC-225cb (300 g; Asahi Glass Co., Ltd, Asahiklin™ AK225), and NaF (44.1 g, 1.05 mol) was added thereto. Then, with stirring the resultant mixture, a fluorine-containing polyether carboxylic acid fluoride (350 g, 0.35 mol) was added dropwise to the mixture, and the mixture was stirred for 2 hrs. The reaction end was determined by NMR via confirming disappearance of the peak of carboxylic acid fluoride. The product was yielded in 347 g, 75.0% yield, and 97.4% purity.

The reaction formula of Example 2 is shown below.

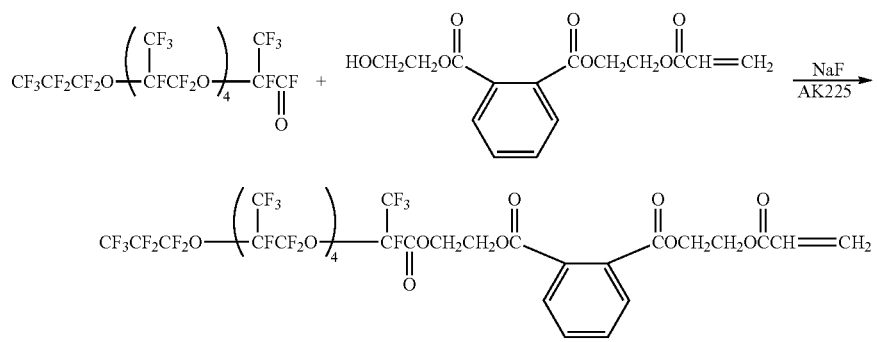

The results of NMR identification on the product of Example 2 are summarized as follows. It was confirmed that the above described reaction of Example 2 proceeded to give a carboxylic acid ester compound of the present invention having the following chemical structure in a high yield.

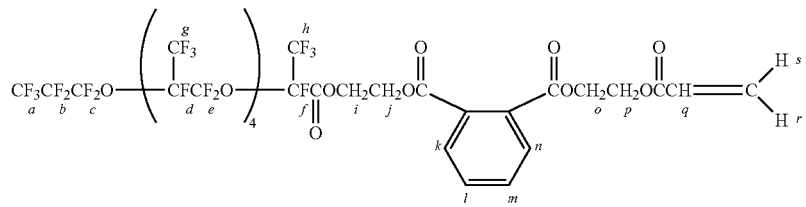

$^{19}$F-NMR [(CD$_3$)$_2$CO, C$_6$F$_6$]

δ (ppm): −143.8; d, −130.1: f, −128.7: b, −85.0 to −77.5: a c, g, e, h $^1$H-NMR [CD$_3$]$_2$CO]

δ (ppm): 4.3-4.7: j, o, p; 4.97: i; 5.9: s, 6.2: r, 6.5: q, 7.5-7.9: k, l, m, n

Example 3

Cyclohexane dimethanol modified acrylate (51 g, 0.26 mol) (Nippon Kasei Chemical Co., Ltd., CHDMA™) was dissolved in a mixed solvent of HCFC-225ca/HCFC-225cb (300 g; Asahi Glass Co., Ltd, Asahiklin™ AK225), and NaF (44.1 g, 1.05 mol) was added thereto. Then, with stirring the resultant mixture, a fluorine-containing polyether carboxylic acid fluoride (345 g, 0.21 mol) was added dropwise to the mixture, and the mixture was stirred for 5 hrs. The reaction end was determined by NMR via confirming disappearance of the peak of carboxylic acid fluoride. The product was yielded in 318 g, 81% yield, and 95.2% purity.

The reaction formula of Example 3 is shown below.

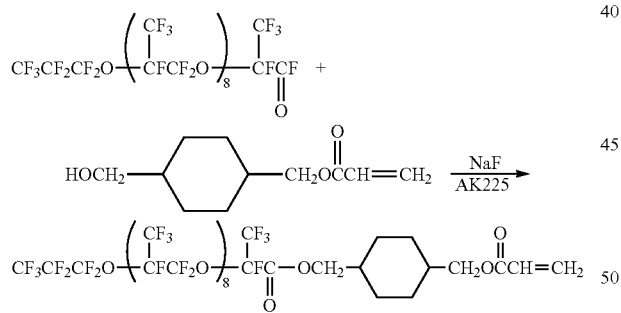

The results of NMR identification on the product of Example 3 are summarized as follows. It was confirmed that the above described reaction of Example 3 proceeded to give a carboxylic acid ester compound of the present invention having the following chemical structure in a high yield.

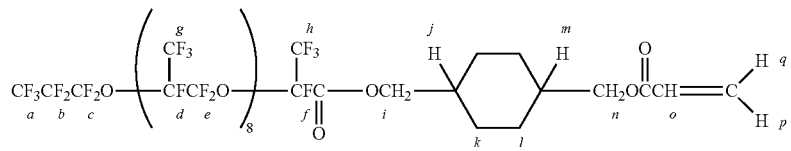

$^{19}$F-NMR [(CD$_3$)$_2$CO, C$_6$F$_6$]

δ (ppm): −143.4; d, −130.1: f, −128.5: b, −85.0 to −76.5: a c, e, g, h $^1$H-NMR [CD$_3$]$_2$CO]

δ (ppm): 1.0-1.5: l, m; 1.5-2.5: j, k; 4.1: n, 4.4: i, 5.9: q, 6.3: p, 6.5: o

The invention claimed is:

1. A carboxylic acid ester compound having a polymerizable functional group and a fluorine atom group, represented by the general formula [I],

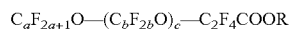

(where a is an integer from 1 to 3; b is an integer from 1 to 4; c is an integer from 0 to 50; and R is represented by the general formula [II],

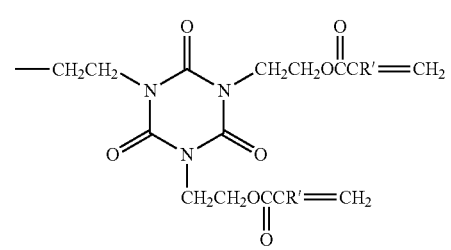

or represented by the general formula [III],

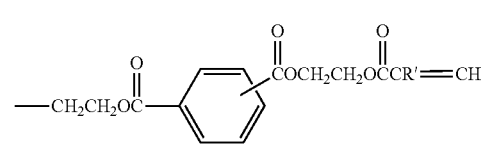

or represented by the general formula [IV],

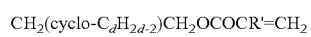

(where R' is a hydrogen atom or a methyl group; and d is an integer from 3 to 6).

2. The method for producing a carboxylic acid ester compound described in claim 1, wherein any one of an isocyanulate derivative represented by the general formula [V], a phthalic acid derivative represented by the general formula [VI] and a cycloalkane dialcohol modified (meth)acrylate represented by the general formula [VII] is made to react with a perfluoropolyether carboxylic acid halide represented by the general formula [VIII],

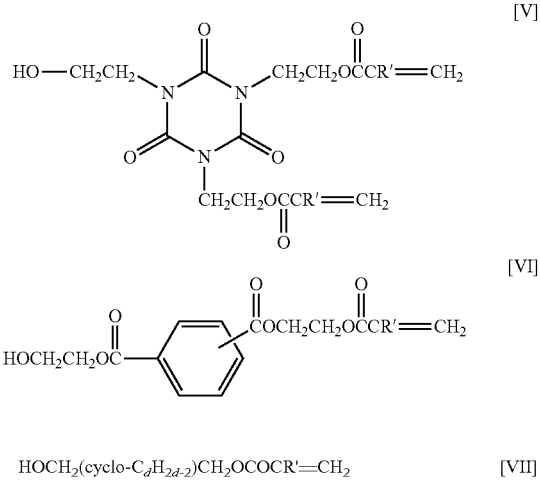

$$C_aF_{2a+1}O-(C_bF_{2b}O)_c-C_2F_4CO-X \qquad [VIII]$$

(where X is a halogen atom; a is an integer from 1 to 3; b is an integer from 1 to 4; and c is an integer from 0 to 50).

3. The method for producing a carboxylic acid ester compound described in claim 2, wherein when any one of the isocyanulate derivative represented by the general formula [V], the phthalic acid derivative represented by the general formula [VI] and the cycloalkane dialcohol modified (meth)acrylate represented by the general formula [VII] is made to react with the perfluoropolyether carboxylic acid halide represented by the general formula [VIII], the reaction is performed in the presence of a hydrogen halide scavenger.

4. The method for producing a carboxylic acid ester compound described in claim 3, wherein an alkaline metal fluoride is used as the hydrogen halide scavenger.

* * * * *